US010617115B2

(12) United States Patent
Ouyang et al.

(10) Patent No.: US 10,617,115 B2
(45) Date of Patent: Apr. 14, 2020

(54) USE OF *PYEMOTES ZHONGHUAJIA* FOR PREPARING BIOLOGICAL CONTROL AGENTS OF *DIAPHORINA CITRI*

(71) Applicants: GUANGDONG INSTITUTE OF APPLIED BIOLOGICAL RESOURCES, Guangzhou, Guangdong (CN); CHANGLI INSTITUTE OF POMOLOGY, HEBEI ACADEMY OF AGRICULTURE AND FORESTRY SCIENCES, Qinhuangdao, Hebei (CN)

(72) Inventors: Gecheng Ouyang, Guangzhou (CN); Lichen Yu, Qinhuangdao (CN); Huilin Lu, Guangzhou (CN); Xiang Meng, Guangzhou (CN); Limin He, Qinhuangdao (CN); Xiaoduan Fang, Guangzhou (CN); Bohua Hou, Guangzhou (CN); Litao Li, Qinhuangdao (CN)

(73) Assignees: GUANGDONG INSTITUTE OF APPLIED BIOLOGICAL RESOURCES, Guangzhou, Guangdong (CN); CHANGLI INSTITUTE OF POMOLOGY, HEBEI ACADEMY OF AGRICULTURE AND FORESTRY SCIENCES, Qinhuangdao, Hebei (CN)

( * ) Notice: Subject to any disclaimer, the term of this patent is extended or adjusted under 35 U.S.C. 154(b) by 99 days.

(21) Appl. No.: 15/760,431

(22) PCT Filed: Dec. 7, 2016

(86) PCT No.: PCT/CN2016/108778
§ 371 (c)(1),
(2) Date: Mar. 15, 2018

(87) PCT Pub. No.: WO2018/049734
PCT Pub. Date: Mar. 22, 2018

(65) Prior Publication Data
US 2019/0059358 A1    Feb. 28, 2019

(30) Foreign Application Priority Data

Sep. 13, 2016  (CN) .......................... 2016 1 0821119

(51) Int. Cl.
*A01M 99/00*  (2006.01)
*A01G 13/00*  (2006.01)
*A01M 17/00*  (2006.01)

(52) U.S. Cl.
CPC ............. *A01M 99/00* (2013.01); *A01G 13/00* (2013.01); *A01M 17/00* (2013.01); *A01M 2200/01* (2013.01)

(58) Field of Classification Search
CPC ..... A01M 17/00; A01M 17/008; A01M 99/00
See application file for complete search history.

(56) References Cited

U.S. PATENT DOCUMENTS 4,646,683 A * 3/1987 Maedgen, Jr. ....... A01K 67/033
                                                    119/6.5
6,235,278 B1 * 5/2001 Miller .................... A01N 63/02
                                                    424/93.2

(Continued)

FOREIGN PATENT DOCUMENTS

CN    101569297 A     11/2009
CN    101889564 A  *  11/2010  ............. A01N 63/00

(Continued)

OTHER PUBLICATIONS

Mass-rearing of Pyemotes zhonghuajia (Prostigmata: Pyemotidae) with substitute hosts. He LiMin et al. Chinese Journal of Biological Control, Chinese Academy of Agricultural Sciences, Beijing, China, Chinese Journal of Biological Control, 2011, vol. 27, No. 2, pp. 165-170 (Year: 2011).*

(Continued)

*Primary Examiner* — Magdalena Topolski
*Assistant Examiner* — Morgan T Barlow
(74) *Attorney, Agent, or Firm* — Westerman, Hattori, Daniels & Adrian, LLP

(57) ABSTRACT

The use of *Pyemotes zhonghuajia* for preparing biological control agents of *Diaphorina citri*. The use of *Pyemotes zhonghuajia* for preparing agents for controlling *Diaphorina citri*. By employing *Pyemotes zhonghuajia* to control *Dia-*

(Continued)

*phorina citri*, it is a biological control method which can avoid the problems caused by chemical pesticides such as environmental pollution, health risk and increased pest resistance to the pesticides.

2 Claims, 2 Drawing Sheets

(56) References Cited

U.S. PATENT DOCUMENTS

| | | | |
|---|---|---|---|
| 6,582,961 B1* | 6/2003 | Moon | A01N 37/16 424/405 |
| 8,327,797 B1* | 12/2012 | Morales-Ramos | A01K 67/033 119/6.5 |
| 10,377,491 B1* | 8/2019 | Fine | B64D 1/16 |
| 2009/0012186 A1* | 1/2009 | Bolckmans | A01K 67/033 514/789 |
| 2009/0205057 A1* | 8/2009 | Bolckmans | A01K 67/033 800/8 |
| 2015/0000600 A1* | 1/2015 | Bolckmans | A01K 67/033 119/6.5 |
| 2015/0030689 A1* | 1/2015 | Bolckmans | A01K 67/033 424/538 |
| 2015/0366177 A1* | 12/2015 | Wackers | A01K 67/033 119/6.5 |

FOREIGN PATENT DOCUMENTS

| | | | | |
|---|---|---|---|---|
| CN | 101935662 A | | 1/2011 | |
| CN | 102696565 A | * | 10/2012 | |
| CN | 102876669 A | | 1/2013 | |
| CN | 104322328 A | | 2/2015 | |
| CN | 106718383 A | * | 5/2017 | |
| EP | 3192366 A1 | * | 7/2017 | ............. A01N 63/00 |
| JP | 2017127301 A | * | 7/2017 | |

OTHER PUBLICATIONS

Xiaoduan Fang, Huilin Lu, Gecheng Ouyang, Yulu Xia, Mingfang et. al. "Effectiveness of Two Predatory Mite Species (Acari: Phytoseiidae) in Controlling Diaphorina citri (Hemiptera: Liviidae)" Florida Entomologist, 96(4): 1325-1333. Dec. 2013. (Year: 2013).*

María Juan-Blasco, Jawwad A. Qureshi, Alberto Urbaneja, and A. Stansly. "Predatory Mite, *Amblyseius swirskii* (Acari: Phytoseiidae), Biological Control of Asian Citrus Psyllid, *Diaphorina citri* (Hemiptera: Psyllidae)" Florida Entomologist, 95(3): 543-551. Sep. 2012. (Year: 2012).*

Zhang et al., "Study on the predatory mites equipped with *Beauveria* sp. for control of Diaphorina ditri", Fujian Agricultural Science and Technology 6 (2011), pp. 72-74, cited in ISR, with English abstract. Publication date Jan. 5, 2011.

Dai et al., "Advances in Biological Control of Citrus Psyllid *Diaphorina citri*, a Vector Insect of Citrus Huanglongbing Disease", Chinese Journal of Biological Control, 2014, 30(3), pp. 414-419, cited in ISR, with English abstract. Publication date Jun. 30, 2014.

* cited by examiner

USE OF *PYEMOTES ZHONGHUAJIA* FOR PREPARING BIOLOGICAL CONTROL AGENTS OF *DIAPHORINA CITRI*

TECHNICAL FIELD

The present invention relates to the field of controlling *Diaphorina citri*, and particular to the use of *Pyemotes zhonghuajia* for preparing biological control agents of *Diaphorina citri*.

BACKGROUND OF THE INVENTION

Huanglongbing, which is a devastating disease of citrus, brings huge economic losses to the global citrus industry and causes great damage in south China as well. Due to the inability to cultivate the bacterium responsible for huanglongbing so far, little is known about the mechanism, and thus it is impossible to directly eradicate the bacterium from the deceased trees at present. As *Diaphorina citri* is an insect vector of huanglongbing, prevention and elimination of *Diaphorina citri* is one key measure for controlling huanglongbing. Due to the lack of cheap and efficient commercial natural enemies, chemical control of *Diaphorina citri* is the major approach. However, large-scale use of the chemical pesticides will not only pollute the environment and do harm to people's health, but also increase pest resistance to the pesticides.

*Pyemotes zhonghuajia*, classified under Subclass Acari, Superorder Acariformes, Suborder Prostigmata and family Pyemotidae of the Class Arachnida, is a predatory mite species found in north China.

SUMMARY OF THE INVENTION

One object of the present invention is to provide the use of *Pyemotes zhonghuajia* for preparing biological control agents of *Diaphorina citri*.

The inventors have found via experiments that *Pyemotes zhonghuajia* showed good effect in controlling *Diaphorina citri*, and thus *Pyemotes zhonghuajia* can be used for preparing biological control agents of *Diaphorina citri*.

The second object of the present invention is to provide a method of controlling *Diaphorina citri*, characterized in that, *Pyemotes zhonghuajia* is released onto a plant with *Diaphorina citri*, and then *Pyemotes zhonghuajia* kills *Diaphorina citri*.

Said plant with *Diaphorina citri* is a host plant or bridging host plant of *Diaphorina citri*.

The inventors have found via experiments that *Pyemotes zhonghuajia* showed good effect in controlling *Diaphorina citri*, and thus *Pyemotes zhonghuajia* can be used for preparing agents for controlling *Diaphorina citri*. The present invention, employing *Pyemotes zhonghuajia* to control *Diaphorina citri*, provides a biological control method which can avoid the problems caused by chemical pesticides such as environmental pollution, health risk and increased pest resistance to the pesticides.

DETAILED DESCRIPTION OF PREFERRED EMBODIMENT

The below embodiment is a specific explanation for the present invention, but not used for limiting the present invention.

Embodiment 1

1. Materials

Insects: *Pyemotes zhonghuajia* (hereinafter referred to as "*pyemotes*") were provided by Changli Institute of Pomology, Hebei Academy of Agriculture and Forestry Sciences. *Diaphorina citri* initial population was collected from Sun Yat-sen University and reared with *Murraya exotica* in insectariums, and the reproduced populations were used in the experiments.

Figure 1:
FIG. 1 shows the laboratory experiment.

Plants: *Citrus reticulata* Blanco cv. Shiyueju (2 to 5 years old) were used in the experiments after cultivated in-house with a same nutrition soil for a certain period 2. Method 2.1 Laboratory Experiment Two potted 2-year-old *Citrus reticulata* Blanco cv. Shiyueju plants, which were similar in shape and size (50 cm in height, and 30 cm in crown width), were pruned to remove the tender shoots, and then placed in transparent cylinders (see FIG. 1). The tops of the cylinders were sealed with 250-mesh screens to prevent escape of *Diaphorina citri* and the *pyemotes*. 40 *Diaphorina citri* adults were used for each plant. After all *Diaphorina citri* settled on the leaves, *pyemotes* contained in a box were placed in one cylinder as the treatment group, while the other plant as the control group was not treated with *pyemotes*. The experiment was conducted in a room maintained at 29±1° C. and about 70% RH. There were 9 replicates for each group. Continuous observation was performed to evaluate the survival of *Diaphorina citri* on each potted plant.

2.2 Field Experiment

Six 5-year-old *Citrus reticulata* Blanco cv. Shiyueju plants (150 cm in height, and 50 cm in crown width) (at 29-35° C. and about 70% RH), each plant having over 200 *Diaphorina citri* adults and nymphs, were not pruned. Boxes containing *pyemotes* were placed on the crotches at the roots of three of the potted plants. The opening of each box was maintained upward so that the *pyemotes* would climb upwards. The other three plants as the control group were not treated. Continuous observation was performed to evaluate the survival of *Diaphorina citri* adults and nymphs on each potted plant.

3. Results 3.1 Laboratory Experiment

On the treated potted plants, death of *Diaphorina citri* was observed one day later, and mortality rose sharply two days later. Four days later, only very few *Diaphorina citri* survived on the treated potted plants, while mortality of *Diaphorina citri* was very low on the potted plants of the control group (see table 1 for detailed results).

TABLE 1

Mortality of *Diaphorina citri* caused by *Pyemotes zhonghuajia*

|  | Treatment | Control | P* |
|---|---|---|---|
| Mortality | 98.06 ± 0.69 | 1.94 ± 0.69 | 0.000 |

*P represents the significance of mean in the paired sample T test (two-tailed test)

3.2 Field Experiment

Figure 2:
FIG. 2 shows *Diaphorina citri* nymphs killed after treated with *Pyemotes zhonghuajia*.
Figure 3:
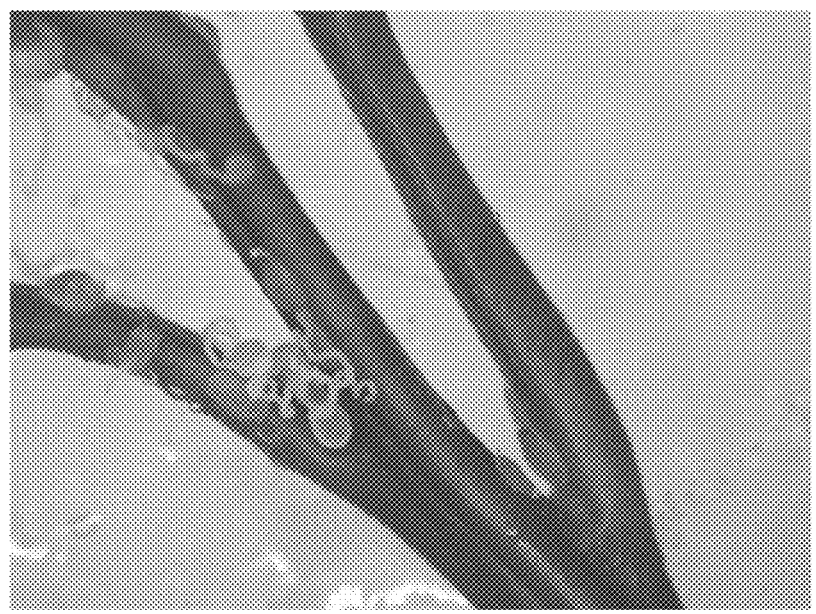
FIG. 3 shows *Diaphorina citri* nymphs not treated with *Pyemotes zhonghuajia*.

The results were as shown in FIG. 2 and FIG. 3. On the three plants treated with *pyemotes*, severe mortality of *Diaphorina citri* adults and nymphs was observed, and one week later the number of surviving *Diaphorina citri* adults decreased significantly, with a reduction of 88%; honeydew excretions of nymphs were hardly observed, and mortality of the nymphs was very high. On the plants not treated with *pyemotes, Diaphorina citri* adults and nymphs survived normally.

The invention claimed is:

1. A method of controlling *Diaphorina citri* on a plant with the *Diaphorina citri*, comprising a step of releasing *Pyemotes zhonghuajia* onto the plant to allow the *Pyemotes zhonghuajia* to kill the *Diaphorina citri*, wherein the plant is placed in a transparent cylinder, a top of the transparent cylinder is sealed with a 250-mesh screen to prevent escape of the *Diaphorina citri* and the *Pyemotes zhonghuajia*, and the *Pyemotes zhonghuajia* is released by placing a box containing the *Pyemotes zhonghuajia* in the transparent cylinder.

2. The method according to claim 1, wherein said plant is a host plant or bridging host plant of *Diaphorina citri.*

* * * * *